(12) United States Patent
Schäfer

(10) Patent No.: US 6,284,547 B1
(45) Date of Patent: Sep. 4, 2001

(54) ON-LINE ANALYSIS OF PROCESS GAS DURING THE PRODUCTION OF KETENE

(75) Inventor: Thomas Schäfer, Heppenheim (DE)

(73) Assignee: Axiva GmbH (DE)

( * ) Notice: Subject to any disclaimer, the term of this patent is extended or adjusted under 35 U.S.C. 154(b) by 0 days.

(21) Appl. No.: 09/463,676

(22) PCT Filed: Jul. 24, 1998

(86) PCT No.: PCT/EP98/04655
§ 371 Date: Jan. 28, 2000
§ 102(e) Date: Jan. 28, 2000

(87) PCT Pub. No.: WO99/08104
PCT Pub. Date: Feb. 18, 1999

(30) Foreign Application Priority Data
Aug. 6, 1997 (DE) .............................. 197 33 837

(51) Int. Cl.[7] ................................................. G01N 1/14
(52) U.S. Cl. ........................................ 436/173; 73/863.84
(58) Field of Search ............................... 436/173; 73/863, 73/864, 42; 356/301, 328; 422/62, 83, 106, 100, 89, 102, 101; 372/92

(56) References Cited

U.S. PATENT DOCUMENTS

| | | |
|---|---|---|
| 3,748,906 * | 7/1973 | Manka . |
| 4,272,481 * | 6/1981 | Ahlstrom, Jr. et al. . |
| 4,779,466 | 10/1988 | Ramsner et al. .................. 73/863.33 |
| 4,800,763 | 1/1989 | Hakkers et al. ........................ 73/863 |
| 5,736,654 * | 4/1998 | Dubois . |
| 5,751,415 * | 5/1998 | Smith et al. . |
| 6,100,975 * | 8/2000 | Smith et al. . |

FOREIGN PATENT DOCUMENTS

| | | |
|---|---|---|
| 0243569 | 11/1987 | (EP) . |
| 0387137 | 9/1990 | (EP) . |

* cited by examiner

*Primary Examiner*—Jill Warden
*Assistant Examiner*—Brian Sines
(74) *Attorney, Agent, or Firm*—Connolly Bove Lodge & Hutz LLP

(57) ABSTRACT

The invention relates to a process for the on-line analysis of a reactive gas mixture, in particular of a gas mixture comprising ketene and/or diketene and/or acetic anhydride and/or acetic acid, which gas mixture is situated in a vessel, which comprises expanding a portion of the gas mixture instantaneously into a sampling line via a probe which is integrated into the vessel and which has an orifice whose clear cross sectional area is less than or equal to 1 mm$^2$ and feeding it to a mass-spectrometric analysis.

10 Claims, 3 Drawing Sheets

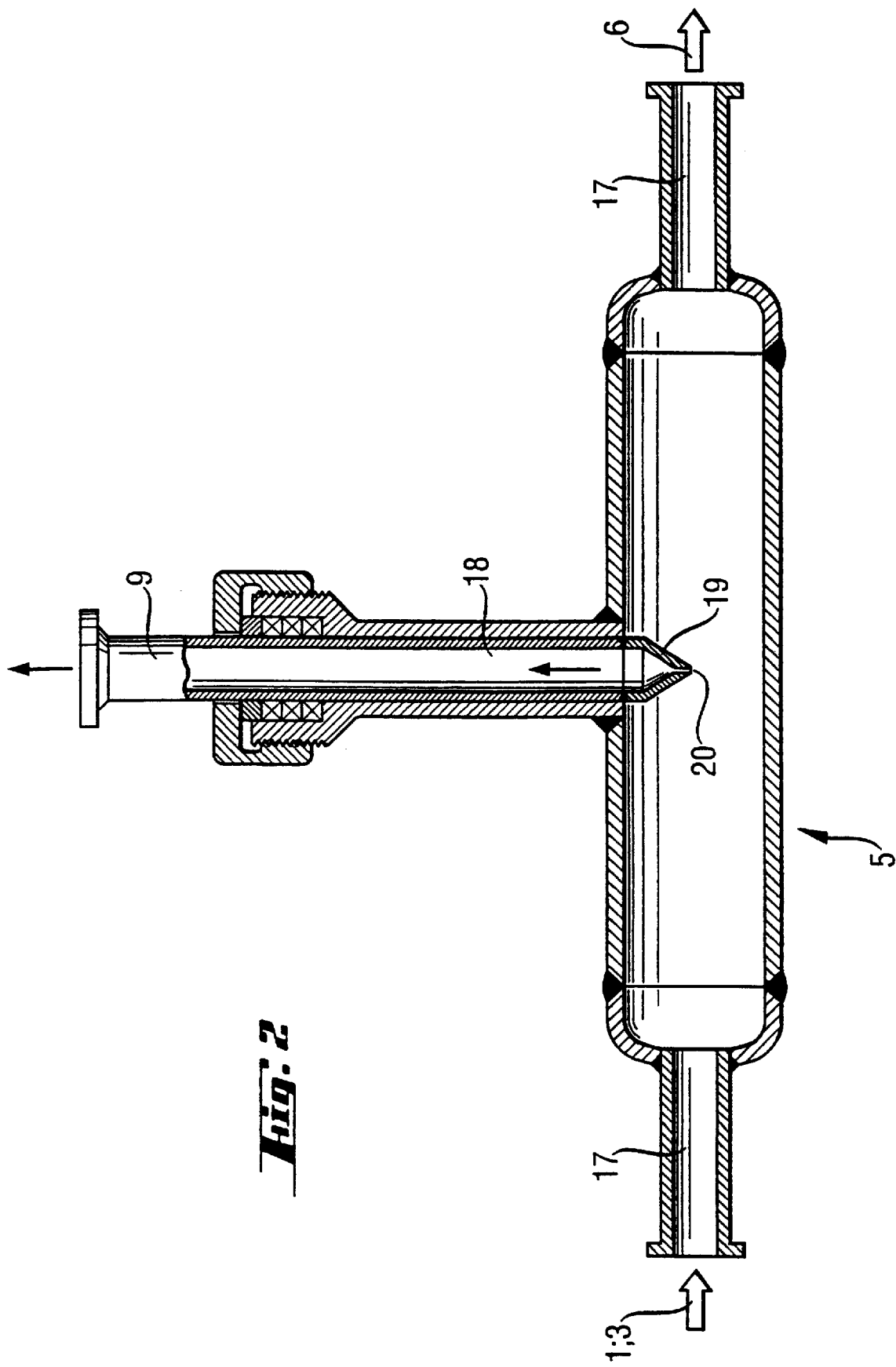

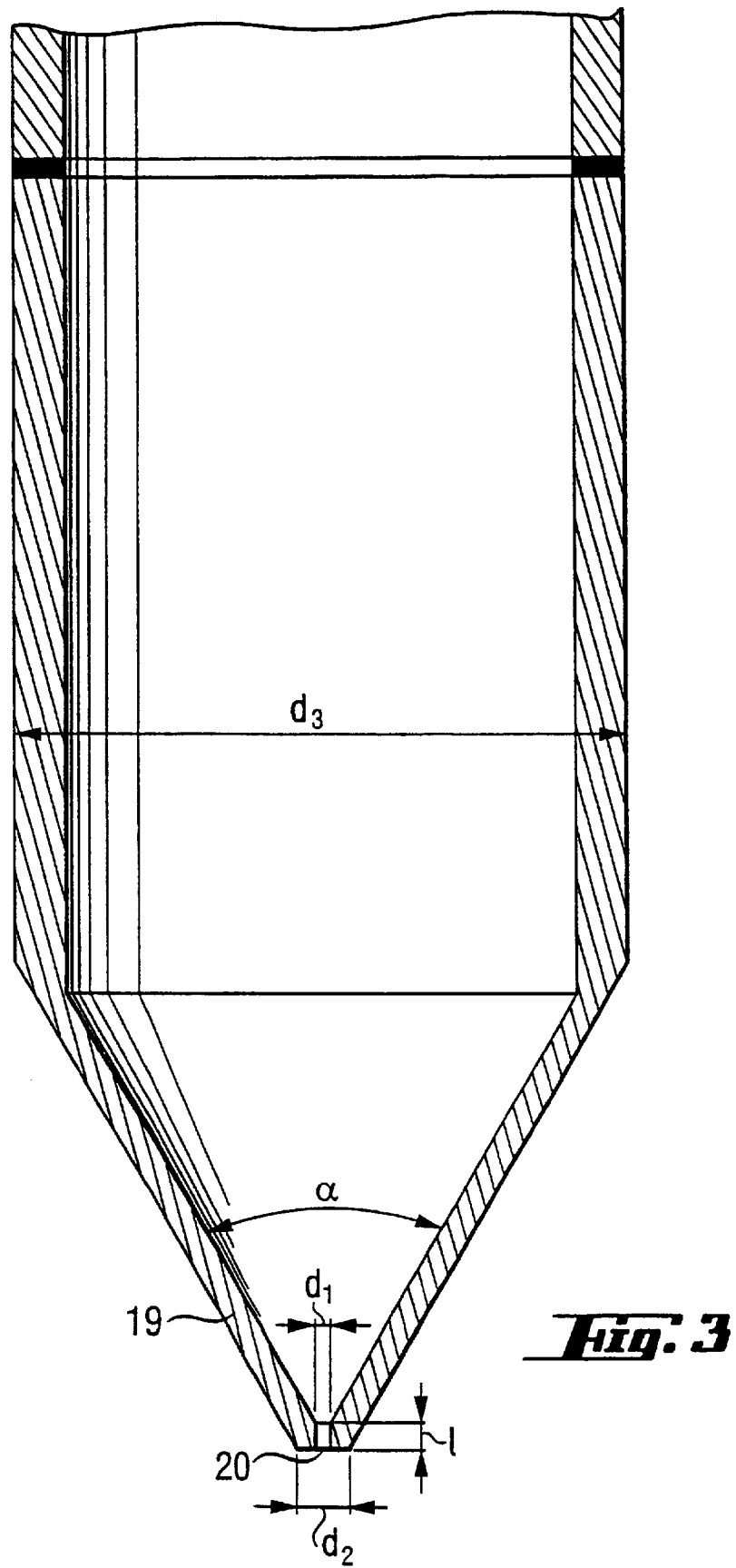

ON-LINE ANALYSIS OF PROCESS GAS DURING THE PRODUCTION OF KETENE

The invention relates to a process for the on-line analysis of a reactive gas mixture, in particular of a gas mixture comprising ketene and/or diketene and/or acetic anhydride and/or acetic acid, which gas mixture is situated in a vessel at a first pressure.

The catalyzed pyrolysis of acetic acid is carried out on an industrial scale for the production of acetic anhydride, diketene and ketene. Ketene is further processed directly to secondary products, e.g. sorbic acid and dimethylacrylolactone. The reaction proceeds at elevated temperatures in the range from 400 to 800°C. and at reduced pressure. In addition to the main products water and ketene, under said reaction conditions, a number of byproducts are formed, e.g. carbon monoxide, carbon dioxide, ethene, ethyne, methane, propadiene and hydrogen. After the reaction, in the further course of the process, unreacted acetic acid and water are condensed out and the process gases are scrubbed with acetic anhydride. The following process steps depend on the target product.

It has not been possible hitherto to analyse such process gases quantitatively. This is due to the high reactivity of the components, which excludes representative sampling and analysis by conventional methods (e.g. GC). The ketene and water formed in the process form acetic acid in a very short time in a reverse reaction, and ketene and acetic acid reform acetic anhydride. In addition, there is the risk of ketene dimerization to form diketene.

The object therefore underlying the invention was to provide a process which permits the on-line analysis of the gas mixture mentioned at the outset. It has now surprisingly been found that the reactive gas mixture described can be analyzed on-line and continuously if a probe having a small orifice diameter is used for drawing off a sample gas stream from the mixture and conducting it via an evacuated sample line to a mass spectrometer for analysis. Over the probe orifice there is thus an instantaneous expansion to a low pressure, which is maintained in the sample line to the mass spectrometer by means of vacuum pumps. There is a further pressure reduction on entry of the gas mixture into the mass spectrometer.

The invention therefore relates to a process for the on-line analysis of a reactive gas mixture in particular of a gas mixture comprising ketene and/or diketene and/or acetic anhydride and/or acetic acid, which gas mixture is situated in a vessel at a first pressure, which comprises expanding a portion of the gas mixture into a sampling line via a probe to a second pressure which is at least ten times lower than the first pressure and feeding it to a mass spectrometer for analysis.

The invention further relates to a process for the on-line analysis of a reactive gas mixture, in particular of a gas mixture comprising ketene and/or diketene and/or acetic anhydride and/or acetic acid, which gas mixture is situated in a vessel, which comprises expanding a portion of the gas mixture instantaneously into a sampling line via a probe which is integrated into the vessel and which has an orifice whose clear cross sectional area is less than or equal to 1 mm$^2$ and feeding it to a mass-spectrometric analysis.

Particular embodiments result from the subclaims.

The probe can be integrated into the vessel or flanged onto it and is preferably fabricated from metal, quartz or ceramic material, and the orifice preferably has a clear cross sectional area between $8 \times 10^{-4}$ and 0.8 mm$^2$ inclusive (e.g. a circular hole having a diameter of 0.01 to 1 mm). The probe is connected via the sampling line to the mass spectrometer. The vacuum can be generated by a pump which delivers a high final vacuum (e.g. a sliding-vane pump). A partial stream of the process gas drawn off is analysed by the mass spectrometer. The mass spectrometer is calibrated in the specific case with certified gas mixtures, by liquids vaporized in the carrier gas and by ketene gas mixtures which are obtained in the laboratory by thermal decomposition of diketene.

The representative sampling of the reactive gas stream is achieved in the specific case of sampling for ketene analysis by an instantaneous expansion from a process condition pressure (100–1000 mbar) to sampling pressure (1–20 mbar) across the small orifice at the probe tip. A pressure reduction by a factor of 100 slows down the reactions by a factor of 10,000 (for second order-reactions). Moreover, owing to the low heat capacity of the expanded process gas, this rapidly cools to room temperature, which leads to a further slowing down of possible reactions in the sampling line. The expansion time depends on the geometry of the probe tip orifice. The expansion proceeds instantaneously, preferably within a time period less than or equal to 0.1 s, particularly preferably within 1 ms to 1 $\mu$s.

Adaptation to higher process pressures, to over 30 bar for example, is possible without difficulty. Heating the sampling line to avoid condensation of components from the process gas is not necessary in the specific case owing to the low pressure in the sampling line. The sampling apparatus used, essentially comprising probe, sampling line and mass spectrometer, can be equipped with pressure sensors, filters, valves and control valves for monitoring and controlling the sampling. A two-stage pressure reduction within the mass spectrometer facilitates control, installation and, in particular, simultaneous operation of a plurality of measurement points.

An exemplary embodiment of the invention is described in more detail below with reference to FIGS. 1, 2 and 3. No restriction in any manner is intended thereby.

In the drawings

FIG. 2 shows a reactor having a sampling probe,

FIG. 3 shows a sketch of the probe tip.

Figure 1:
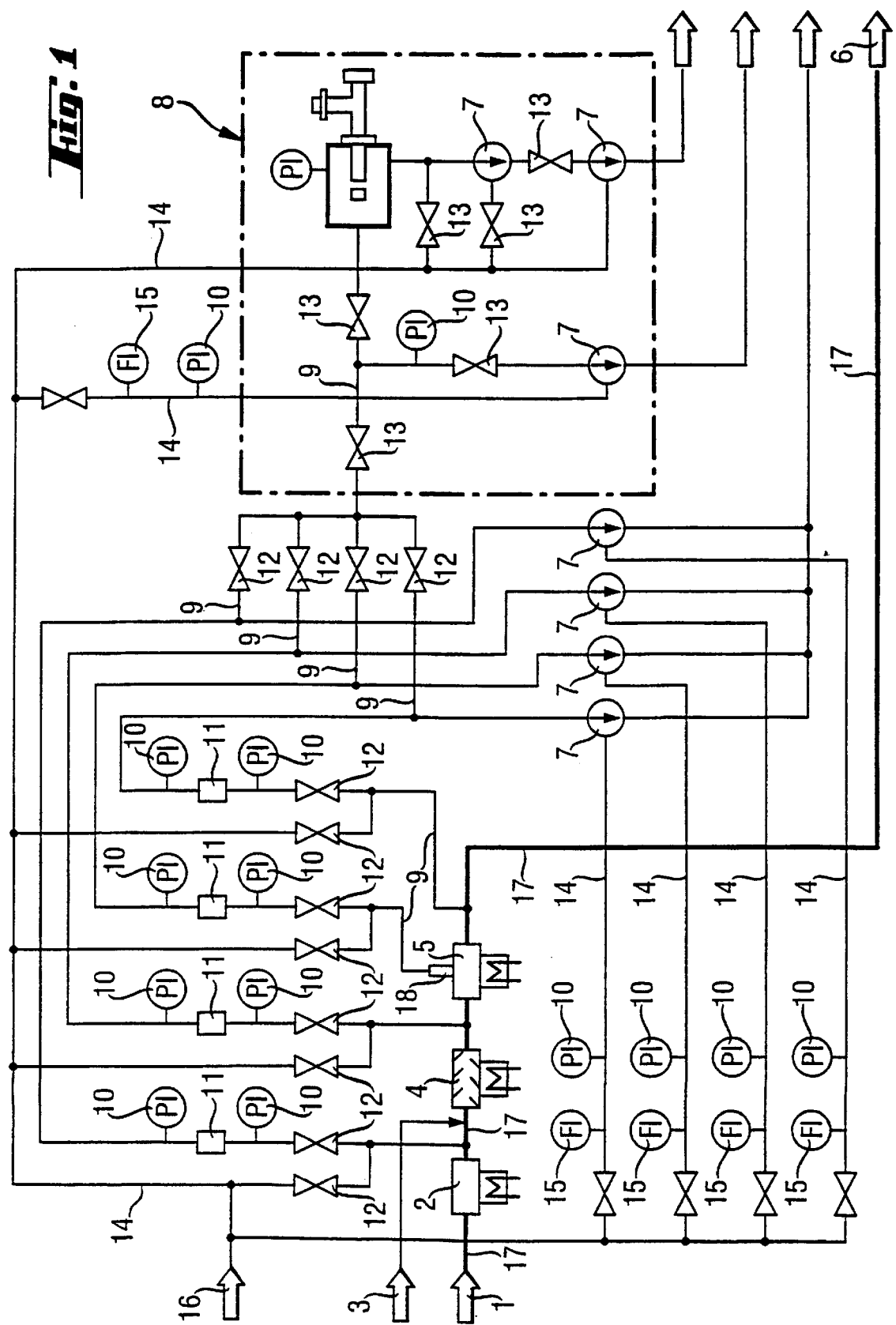
FIG. 1 shows a simplified process flow diagram.

According to FIG. 1, acetic acid 1 is heated in a preheater 2, then admixed with a catalyst 3, intensively mixed with the catalyst 3 in a heated mixer 4 and reacted in a heated reactor 5. The resulting reaction mixture 6 is withdrawn from the reactor 5. Upstream of the mixer 4, upstream, out of and downstream of the reactor 5, samples are withdrawn from the process gas streams by means of pumps 7 and via probes 18 (only shown in the drawing for the reactor 5) and fed to a mass spectrometer 8 for analysis. The system of sampling lines 9 is equipped with pressure sensors 10, filters 11, valves 12 and control valves 13 for monitoring and controlling the sampling. Likewise, the system of lines 14 for flushing with nitrogen 16.

The pumps 7, for explosion protection, are flushed with nitrogen 16, and the nitrogen flow rate is monitored by flow meters 15. The pressure downstream of the flow meter 15 is monitored by a pressure sensor 10. The process substances 1, 3 are conducted in the pipe system 17. FIG. 2 shows a reactor 5 which is designed as a tubular reactor and into which a sampling probe 18 is built in. The probe 18 essentially consists of a tube having a truncated conical probe tip 19 which has a small orifice 20.

FIG. 3 shows an embodiment according to the invention of the probe tip in the form of a truncated cone having an angle $\alpha$ of preferably 60°, a borehole having a diameter d1 of preferably 0.3 mm and a length l of preferably 0.5 mm. The outer diameter d2 at the end of the truncated cone is preferably 1 mm. The diameter d3 at the base of the truncated cone is matched to the geometry of the sampling line.

Test measurements in systems of this type for acetic acid pyrolysis were carried out successfully on an operational and pilot-plant scale downstream of the stages preheating, catalyst metering, reactor, condensation, acetic anhydride scrubbing and downstream of compression of the process gases. The diameter of the probe orifice, depending on the sampling point, was 100, 200, 300 or 500 µm, corresponding to a process gas pressure between 100 and 1100 mbar. The pressure downstream of the tip of the probe after expansion was between 2 and 20 mbar and the pressure at the mass spectrometer inlet system was 1 to 5 mbar. The mass spectrometer was operated continuously. The time between two analyses was about 1 min. The apparatus for sampling, the selection and switching between measurement points was automated. Surprisingly, in these measurements, a high service life of the probes used of several months in continuous operation was found. A postulated rapid blockage of the probes by particles in the gas stream, or coking of the probe as a result of gas reactions, which would have excluded use, did not occur, possibly owing to the high shear forces at the probe tip due to the process gas stream and the design according to the invention of the probe tip.

The advantages of the process according to the invention are essentially that the gas phase composition can be determined completely, quantitatively, highly accurately and on-line at any desired point of the production process. Further advantages are the low level of interference with the process owing to the use of miniaturized probes, the low sample gas volume required (<10 l (S.T.P.)/h) and the low maintenance requirement. Quantitative determination of the process gas composition is required to improve process monitoring and control and, due to improved knowledge of the process, opens up considerable potential savings. Furthermore, the apparatus can also be used in general in other processes for representative sampling of reactive and/or corrosive process gases.

Possible other applications are: analysis of the process gases of all production, laboratory and pilot plants in which ketene and/or acetic acid are reacted, e.g. acetic acid pyrolysis, preparation of ketene secondary products and acetic acid (sorbic acid and dimethylacrylolactone), monitoring of the starting material streams, sampling and analysis of reactive and/or corrosive gas mixtures in any processes. A suitable apparatus for sampling can be adapted to altered pressure and temperature conditions with low expenditure.

What is claimed:

1. A process for the on-line analysis of a reactive gas mixture in particular of a gas mixture comprising ketene and/or diketene and/or acetic anhydride and/or acetic acid, which gas mixture is situated in a vessel at a first pressure, which comprises expanding a portion of the gas mixture into a sampling line via a probe to a second pressure which is at least ten times lower than the first pressure in order to slow down the reactions of the reactive gas mixture and feeding it to a mass spectrometer for analysis where a further pressure reduction is performed on entry of the gas mixture into the mass spectrometer.

2. The process as claimed in claim 1, wherein the second pressure is at least 20 times, preferably at least 100 times, lower than the first pressure.

3. The process as claimed in claim 1, wherein the expansion is performed within a time period less than or equal to 0.1 s, preferably within 1 ms to 1 µs.

4. The process as claimed in claim 1, wherein the second pressure is between 0.1 and 100, preferably between 1 and 10, particularly preferably between 3 and 5, mbar.

5. The process as claimed in claim 1, wherein the expansion to the second pressure is performed via a probe which is integrated into the vessel and has an orifice whose clear cross sectional area is less than or equal to 1 mm.

6. The process as claimed in claim 5, wherein the clear cross sectional area is between 0.0001 and 0.5 inclusive, preferably between 0.001 and 0.1 inclusive, mm.

7. The process as claimed in claim 5, wherein the probe is fabricated from metal or quartz or ceramic material.

8. The process as claimed in claim 5, wherein the sample gas flow rate is less than 10 l(S.T.P.)/h, particularly preferably between 1 and 5 l(S.T.P.)/h.

9. The use of a mass spectrometer for carrying out the process as claimed in claim 1.

10. The use of a probe which has an orifice whose clear cross sectional area is less than or equal to 1 $mm^2$ for carrying out the process as claimed in claim 1.

* * * * *

UNITED STATES PATENT AND TRADEMARK OFFICE
CERTIFICATE OF CORRECTION

PATENT NO.   : 6,284,547 B1
DATED        : September 4, 2001
INVENTOR(S)  : Thomas Schäfer It is certified that error appears in the above-identified patent and that said Letters Patent is hereby corrected as shown below:

Column 4,
Line 30, "mm" should read -- $mm^2$ --.
Line 33, "mm" should read -- $mm^2$ --.

Signed and Sealed this

Twelfth Day of March, 2002

Attest:

JAMES E. ROGAN
*Attesting Officer*     *Director of the United States Patent and Trademark Office*